United States Patent

Crawford

[11] Patent Number: 5,973,010
[45] Date of Patent: Oct. 26, 1999

[54] COMPOSITION FOR HEALING SKIN WOUNDS

[76] Inventor: Robert L. Crawford, P.O. Box 56101, Phoenix, Ariz. 85079-6101

[21] Appl. No.: 09/079,623

[22] Filed: May 15, 1998

[51] Int. Cl.⁶ .................. A61K 31/095; A61K 31/10; A61K 31/13; A61K 33/04

[52] U.S. Cl. .................. 514/709; 514/438; 514/553; 514/554; 514/557; 514/558; 514/560; 514/706; 514/708; 514/710; 514/711; 514/740; 514/762; 514/863; 514/861; 514/886; 514/887; 424/43; 424/44; 424/665; 424/709; 424/715; 424/716; 424/717; 424/DIG. 13

[58] Field of Search .................. 514/438, 553, 514/554, 557–558, 560, 706, 708–711, 740, 762, 863, 861, 886, 887; 424/43, 44, 709, 715–717, DIG. 13, 665

[56] References Cited

U.S. PATENT DOCUMENTS

| 4,401,651 | 8/1983 | Knutson | 424/78.06 |
| 4,788,061 | 11/1988 | Shore | 514/50 |
| 4,804,651 | 2/1989 | Duvic et al. | 514/50 |

OTHER PUBLICATIONS

Martindale The Extra Pharmacopoeia, 13th edition, The Pharmaceutical Press, London, 1993, pp. 756 and 1646 (Inotyol).

*Primary Examiner*—John Pak
*Attorney, Agent, or Firm*—Tod R Nissle P.C.

[57] ABSTRACT

A composition and method for treating epidermal wounds utilizes an aqueous solution of sodium sulphate, sodium carbonate, sodium bicarbonate, sodium chloride and ichthammol.

2 Claims, No Drawings

COMPOSITION FOR HEALING SKIN WOUNDS

This invention relates to pharmaceutical healing compositions.

More particularly, the invention relates to a composition which facilitates the healing of epidermal wounds.

A wide variety of antiseptic and other compositions have been utilized to facilitate the healing of epidermal wounds, infections, irritations, and diseases. Many of such compositions have proven effective and useful. However, circumstances still arise in which few, if any, compositions are effective in healing the skin. In some instances, the cause of an epidermal infection or wound is difficult to ascertain and, as a result, determining the proper treatment for the wound is concomitantly difficult. In other cases, for instance psoriasis or eczema, the disease is known, but methods or compositions for effectively treating the disease may not be readily available.

Accordingly, it would be highly desirable to provide an improved composition and method for treating psoriasis, eczema, and for, in general, treating skin wounds and infections in human beings and animals.

I have discovered an improved composition and method for treating epidermal wounds, infections, and diseases. The improved composition and method has provided surprising and unexpected results and has proved effective in treating psoriasis, eczema, and wounds which did not respond to conventional pharmaceutical compositions and treatment methods.

In accordance with one embodiment of the invention, I provide an improved aqueous solution for facilitating the healing of a wound in the skin. The aqueous solution includes in each gallon of water from 0.01 to 0.45 pounds of sodium sulphate; from 0.015 to 0.54 pounds of sodium carbonate; from 0.005 to 0.20 pounds of sodium bicarbonate; from 0.01 to 0.32 pounds of sodium chloride; and, from 0.00035 to 0.025 pounds of ichthammol.

In another embodiment of the invention, I provide an improved method for treating 5 a wound in the skin to facilitate healing the wound. The improved method includes the step of providing an aqueous solution. The solution includes in each gallon of water from 0.01 to 0.45 pounds of sodium sulphate; from 0.015 to 0.54 pounds of sodium carbonate; from 0.005 to 0.20 pounds of sodium bicarbonate; from 0.01 to 0.32 pounds of sodium chloride; and, from 0.00035 to 0.025 pounds of ichthammol. The improved method also includes the step of applying the aqueous solution to the wound. A minor effective amount of the aqueous solution ordinarily is applied to the wound. A minor effective amount of the solution comprises an amount sufficient to coat and/or wet the wound. In the case of psoriasis, an amount of the solution effective to wet the dry skin produced by the psoriasis is applied. In the case of a cut or other wound, once the wound has stopped bleeding, an amount of solution sufficient to coat the wound is applied. Any desired procedure for applying the aqueous solution can, however, be utilized. For example, if a patient has psoriasis over large areas of his or her body, it is sometimes advantageous to fill a bathtub with the aqueous solution and to soak in the solution for one or more minutes. The aqueous solution is usually maintained at room temperature during storage and during application of the solution to the skin, but can be warmed to temperatures which are not uncomfortable to the epidermis of a patient.

The aqueous solution of the invention is prepared by admixing all of the ingredients noted above except ichthammol in water. This solution is then heated to boiling and the ichtammol is admixed, after which the resulting solution is cooled to room temperature.

The following examples are given by way of illustration and not to limit the scope of the invention. The examples illustrate surprising results which have been obtained by utilizing the composition of the invention when other convention skin treatments have been attempted and have failed in connection with treating the wounds in the skin of animals and human beings.

EXAMPLE 1

Twenty-one gallons of an epidermal treatment composition (ETC) was prepared. The first step in preparing the ETC was to admix 0.35 pound of sodium sulphate, 0.44 pound of sodium carbonate, 0.14 pound of sodium bicarbonate, and 0.26 pound of sodium chloride for each gallon of water to form an aqueous sodium reaction solution. The aqueous sodium reaction solution was heated to a boil and 0.01 pound of ichthammol per each gallon of water was admixed to the sodium reaction solution to form the ETC. The ETC was cooled to room temperature.

EXAMPLE 2

Twelve ounces of the ETC was poured into an empty gallon container and the remaining volume of the container was then completely filled with water. The container was shaken to admix the ETC and water to form a wound treatment solution (WTS).

EXAMPLE 3

A black pony boarded at a stable had a severe open wound through the skin on the side of its face. The wound covered an area of about four inches by four inches and emitted a disagreeable odor. At its deepest point, the wound was about one-half inch deep. An individual who also boarded her horses at the stable stated that she thought nothing could be done to help the pony. The owner of the pony indicated that a veterinarian had examined the pony's wound and that, to the best of the owner's recollection, the veterinarian had indicated that it was likely the pony had a cancer and that nothing could be done for the pony.

The pony was treated by its owner with each of the below listed compositions. At least several applications of each of the compositions was utilized without success before the next one of the compositions was utilized or until the owner gave up attempting to cure the wound.

| | Composition | Ingredients per Label |
|---|---|---|
| a. | Scarlet Oil (TM) | Isopropyl alcohol (32% V/V), biebrich scarlet. |
| b. | Swat Salve (TM) | Pieronyl or Butoxide Technical 0.5%, 1 and N 0.02%, Di-N-Propyl isoconeronate 1.0%. |
| c. | Bag Balm (TM) | 8-Hydroxy, Quindine Sulfate 0.3% in a Petrolatum, Lanolin Base, |
| d. | BETADINE (TM) Solution | Citric acid, dibasic sodium phosphate, glycerin. |
| e. | FURA (TM) Dress | 0.27% Nitrofurazone in a water soluble base of polyethylene gycol. |
| f. | Iodine | Iodine. |
| g. | Hydrogen Peroxide | H2O2 (3% aqueous solution). |
| h. | FURRALL (TM) Spray | N/A. |
| i. | BLU KOTE (TM) | Sodium propionate, gentian violet, acriflavine in a special base of water urea. Glycerine, isopropyl alcohol 47% by |

| Composition | Ingredients per Label |
|---|---|
| | volume. |

None of the above-listed compositions caused the wound to heal. The size and severity of the wound appeared unchanged after each of the compositions was utilized. One result of treating the pony with all of the above compositions was that the pony was extremely shy and sensitive and did not want anyone near the wound on its face. The pony would throw or move its head away from anyone or anything that attempted to get in close proximity of the wound.

The WTS of Example 2 was placed in a spray bottle. Beginning on or about Dec. 11, 1997, an amount of WTS sufficient to wet the wound was sprayed on the pony's open wound twice a day. The wound began to heal. On the morning of Dec. 11, 1997, the pony resisted being sprayed with the WTS for the first time. However, when the time came for the WTS to again be applied during the afternoon of Dec. 11, 1997, the pony saw the spray bottle (that had been used to apply the WTS on the morning of Dec. 11, 1997), did not shy away from the bottle, did not move its head, and stood as if it wanted to again be sprayed with the WTS. This indicated that the pony had received immediate relief from the WTS.

On Dec. 21, 1997, the pony's face was examined. An amount of WTS sufficient to wet the wound had continued to be sprayed on the wound twice a day from Dec. 11 to Dec. 21, 1997. The wound was healing and appeared to be only one-quarter of an inch deep.

On Jan. 4, 1998, the pony's face was examined. An amount of WTS sufficient to wet the wound had continued to be sprayed on the wound twice a day from Dec. 21, 1997 to Jan. 4, 1998. The wound had further decreased in size and was about two inches long and one inch wide at its greatest extents. The depth of the wound was only about one-eighth of an inch. Hair had grown back in the areas where the wound had healed.

On Jan. 18, 1998, the pony's face was examined. An amount of WTS sufficient to wet the wound had continued to be sprayed on the wound twice a day from Jan. 4 to Jan. 18, 1998. The wound had further decreased in size.

On Feb. 20, 1998, the pony's face was examined. An amount of WTS sufficient to wet the wound had continued to be sprayed on the wound twice a day from Jan. 18, 1998 to Feb. 20, 1998. The wound was completely closed and the pony's hair had grown back completely except for an area about one-quarter of an inch long.

EXAMPLE 4

A Caucasian women had eczema on the skin on her hands and had utilized unsuccessfully a variety of pharmaceutical products in an attempt to heal the eczema.

The woman began applying to the eczema once or twice a day an amount of the WTS sufficient to wet the eczema. After seven days, it was visibly evident that the eczema was healing.

After several weeks of the daily treatment, the eczema was much improved and the daily treatment was continued.

EXAMPLE 5

A nine year old boy had four patches of psoriasis on the skin on the top of his head. Each patch was about one inch across at its greatest extent.

An amount of WTS sufficient to wet each patch of psoriasis in its entirety was applied once or twice daily.

After seven days of the daily treatment it was evident that the psoriasis was healing.

After about eight weeks of the daily treatment, the psoriasis was completely healed and the daily treatment was discontinued.

During the two months following the discontinuation of the daily treatment, there was no reoccurrence of the psoriasis.

EXAMPLE 6

A Caucasian woman had a split in the skin on the tip or the "fingerprint pad" of the thumb of her right hand. The split was about one-half of an inch long, about one-sixteenth of an inch wide and deep, and appeared to extend completely through the epidermis, dermis, and subcutaneous tissue to the muscle underlying the skin. The split was inflamed and caused the woman pain. The woman's doctor indicated that he thought the split in her skin could be caused by a fungus.

The woman wet the inner exposed surfaces of the split with WTS. Within twenty to thirty minutes, the pain caused by the split was gone. By the morning of the next day, the split had closed and a scab had formed along the top edges of the split. The woman was still not experiencing any pain produced by the split. After several days the split had healed.

EXAMPLE 7

A Caucasian male in his fifties had spots of psoriasis on the skin on his hands. Each spot was about one-quarter to one inch wide.

The man began applying to the psoriasis once or twice a day an amount of the WTS sufficient to wet each psoriasis patch. After seven days, it was evident that the psoriasis was healing.

After several weeks of the daily treatment, the psoriasis was completely healed.

EXAMPLE 8

A 50 year old Caucasian male has a pair of one-half inch long paper cuts in the skin of his left hand. Each cut is about one-thirty second of an inch deep and is painful.

The cuts are washed with soap and water and the left hand is dried. After the left hand was dried, each cut was still painful.

One of the cuts is treated at room temperature of 76 degrees F. with WTS to wet the inner surfaces of the cut. Within twenty to thirty minutes the pain ceases in the cut treated with WTS. The other cut (which is not treated with WTS) continues to produce pain.

The cut treated with WTS seals shut and heals in about two days. There is no recurrent pain in this cut.

The cut not treated with WTS seals shut and heals in about four days. The cut not treated with WTS continues to produce pain for a day after being washed as described above.

EXAMPLE 9

A six year old quarter horse has a pair of one inch long, one-sixteenth of an inch deep, and one-sixteenth of an inch wide cuts in his upper front leg.

The cuts are washed with soap and water and dried.

One of the cuts is treated at room temperature of 76 degrees F. with WTS to wet the inner surfaces of the cut.

The cut treated with WTS seals shut and forms a scab in about two days.

The cut not treated with WTS seals shut and forms a scab in about four days.

EXAMPLE 10

A four year old female German Shepherd dog has a pair of one inch long, one-sixteenth of an inch deep, and one-sixteenth of an inch wide cuts in her back above her right front leg.

The cuts are washed with soap and water and dried.

One of the cuts is treated at room temperature of 76 degrees F. with WTS to wet the inner surfaces of the cut.

The cut treated with WTS seals shut and forms a scab in about two days.

The cut not treated with WTS seals shut and forms a scab in about four days.

EXAMPLE 11

Examples 3 to 10 are repeated, except that ETS is utilized in place of WTS. Similar results are obtained.

EXAMPLE 12

Example 2 is repeated, except that only one-half gallon of water is admixed with twelve ounces of ETS to produce the WTS.

EXAMPLE 13

Examples 3 to 10 are repeated, except that the WTS of Example 12 is utilized, which WTS is produced by admixing one-half gallon of water with twelve ounces of ETS. Similar results are obtained.

Having described my invention in such terms as to enable those skilled in the art to understand and practice it, and having identified the presently preferred embodiments thereof, I claim:

1. A aqueous solution for facilitating the healing of a wound in the skin, said composition comprising in each gallon of water (a) from 0.01 to 0.45 pounds of sodium sulphate;
(b) from 0.015 to 0.54 pounds of sodium carbonate;
(c) from 0.005 to 0.20 pounds of sodium bicarbonate;
(d) from 0.01 to 0.32 pounds of sodium chloride; and,
(e) from 0.00035 to 0.025 pounds of ichthammol.

2. A method for treating a wound in the skin to facilitate healing of the wound, comprising the steps of (a) providing an aqueous solution comprising in each gallon of water
 (i) from 0.01 to 0.45 pounds of sodium sulphate;
 (ii) from 0.015 to 0.54 pounds of sodium carbonate;
 (iii) from 0.005 to 0.20 pounds of sodium bicarbonate;
 (iv) from 0.01 to 0.32 pounds of sodium chloride; and,
 (v) from 0.00035 to 0.025 pounds of ichthammol; and
(b) applying an effective amount of said aqueous solution to said wound.

* * * * *